(12) United States Patent
Yang et al.

(10) Patent No.: US 10,526,258 B2
(45) Date of Patent: Jan. 7, 2020

(54) PROCESS FOR PRODUCING BUTADIENE BY OXIDATIVE DEHYDROGENATION OF BUTYLENE

(71) Applicant: WISON ENGINEERING LTD., Shanghai (CN)

(72) Inventors: Wenshu Yang, Shanghai (CN); Yongjun Wu, Shanghai (CN); Yansheng Li, Shanghai (CN)

(73) Assignee: WISON ENGINEERING LTD., Shanghai (CN)

( * ) Notice: Subject to any disclaimer, the term of this patent is extended or adjusted under 35 U.S.C. 154(b) by 0 days.

(21) Appl. No.: 15/599,570

(22) Filed: May 19, 2017

(65) Prior Publication Data
US 2018/0086679 A1    Mar. 29, 2018

(30) Foreign Application Priority Data
Sep. 23, 2016  (CN) .......................... 2016 1 0844599

(51) Int. Cl.
*C07C 5/48* (2006.01)
*C07C 5/42* (2006.01)
*C07C 5/00* (2006.01)

(52) U.S. Cl.
CPC ............ *C07C 5/48* (2013.01); *C07C 2523/02* (2013.01); *C07C 2523/745* (2013.01);
(Continued)

(58) Field of Classification Search
CPC .... C07C 5/48; C07C 5/44; C07C 5/42; C07C 5/00
See application file for complete search history.

(56) References Cited

U.S. PATENT DOCUMENTS

2016/0023963 A1* 1/2016 Maat .................. C07C 5/48
585/329

FOREIGN PATENT DOCUMENTS

| CN | 101367702 A | 2/2009 |
|---|---|---|
| CN | 102516008 A | 6/2012 |

(Continued)

OTHER PUBLICATIONS

CN103964998A_English (a machine translated English document) (Year: 2014).*

*Primary Examiner* — Youngsul Jeong
(74) *Attorney, Agent, or Firm* — Scully Scott Murphy & Presser (57) ABSTRACT

The present invention provides a process for producing butadiene by oxidative dehydrogenation of butylene, comprising: a reaction stage, wherein a multi-stage adiabatic fixed bed in series is used, wherein butylene, oxygen-comprising gas and water are reacted in the presence of a catalyst in each stage of the adiabatic fixed bed with the first stage of the adiabatic fixed bed being further separately fed a diluent, being nitrogen and/or carbon dioxide, and the molar ratio between this separately fed diluents and the oxygen of all the oxygen-comprising gases fed in the subsequent stage(s) of the adiabatic fixed bed being controlled, wherein the oxygen-comprising gas is air, oxygen-enriched air or oxygen, and at least one of all the oxygen-comprising gases fed in the subsequent stage(s) of the adiabatic fixed bed is oxygen-enriched air having a specific oxygen concentration or oxygen; and a post treatment stage, wherein the effluent from the last stage of the adiabatic fixed bed is treated to obtain a product butadiene. The present invention has an advantage that the whole process is with reduced total energy consumption.

9 Claims, 4 Drawing Sheets

Two axial adiabatic fixed beds in series (52) U.S. Cl.
CPC .... *C07C 2523/755* (2013.01); *C07C 2523/78* (2013.01); *C07C 2527/185* (2013.01)

(56) References Cited

FOREIGN PATENT DOCUMENTS

| | | | | |
|---|---|---|---|---|
| CN | 103964996 A | | 8/2014 | |
| CN | 103964998 A | * | 8/2014 | ............. C07C 11/16 |
| CN | 103964998 A | | 8/2014 | |
| CN | 104772081 A | | 7/2015 | |

* cited by examiner

Fig.1 Two axial adiabatic fixed beds in series

Fig.2 Two axial adiabatic fixed beds with an intermediate feed quench

Fig.3 First radial adiabatic fixed bed and second axial adiabatic fixed bed with an intermediate feed quench Fig.4 First axial-radial adiabatic fixed bed and second radial adiabatic fixed beds with an intermediate feed quench

PROCESS FOR PRODUCING BUTADIENE BY OXIDATIVE DEHYDROGENATION OF BUTYLENE

FIELD OF THE INVENTION

The present invention is related to a process for producing butadiene by oxidative dehydrogenation of butylene, particularly to a process for producing butadiene by oxidative dehydrogenation of butylene using an adiabatic fixed bed.

BACKGROUND

Butadiene is an important basic raw material in the petrochemical industries, and is widely used in the production of many synthetic rubbers, including polybutadiene rubber, styrene-butadiene rubber, butadiene-acrylonitrile rubber and butadiene rubber, wherein polybutadiene rubber is a main material for the production of tyres. Furthermore, butadiene is widely used in the syntheses of resins, fibers and fine chemical products. For example, butadiene can be used in the production of many coatings.

In the prior art, butadiene was ever produced mainly by separating C4 fractions, which were main by-products from the production of ethylene through hydrocarbon cracking. However, in recent years, with the change in the structure of the energy sources, C1 chemical industry, shale gas and the like were developed soon so that the production of butadiene from hydrocarbon cracking was reduced gradually, whereas the downstream industries of butadiene were developed soon so that the demand of butadiene was increased continuously. In such a situation, the process for producing butadiene by oxidative dehydrogenation of butylene was developed and more and more attention was attracted gradually.

In the oxidative dehydrogenation butylene is oxidized and dehydrogenated with oxygen to form butadiene in the presence of a catalyst, and the resultant product comprises butadiene as the primary product and some by-products such as carbon dioxide, carbon monoxide, hydrogen and oxygenates including aldehydes, ketones, acids and the like. Due to the presence of the by-products, the resultant product needs to be post-treated, including first heat recovery and water scrubbing to recover the reaction heat and remove most oxygenates, then compression (generally multi-stage compression) and oil absorption-desorption to separate raw butadiene, and final butadiene extraction to obtain finished butadiene suitable for industries subsequently.

The suitable reactors for oxidative dehydrogenation of butylene generally comprise a fluidized bed and an adiabatic fixed bed, wherein the fluidized bed has a problem that the catalyst used therein may have to be strong enough to resist the abrasion during the fluidization, whereas the adiabatic fixed bed has more simple requirements for the catalyst, thus being widely used in the oxidative dehydrogenation of butylene.

When being used in the oxidative dehydrogenation of butylene to butadiene, the adiabatic fixed bed is generally in the form of multi-stage adiabatic fixed bed, typically of two- or three-stage adiabatic fixed bed, wherein butylene, water and oxygen-comprising gas as the feed are reacted over the catalyst. In such a situation, in order to control the temperature in the catalyst bed within a suitable range, a lot of steam is needed, so high energy consumption is necessary.

CN101367702A disclosed a process for producing butadiene by oxidative dehydrogenation of butylene using an axial fixed bed, wherein a two-stage axial fixed bed is used to produce butadiene from a feed comprising butylene, air and steam, wherein an intermediate heat exchanger is provided between the two stages of the fixed bed to heat the steam to the first stage of the fixed bed through heat exchanging with the effluent from the first stage of the fixed bed.

CN102516008A disclosed a new process for oxidative dehydrogenation, wherein a two-stage fixed bed is used to produce butadiene from a feed comprising butylene, steam and oxygen-enriched air, wherein the conversion of butylene is improved by the oxygen-enriched air, and the effluent from the reactor has a reduced nitrogen amount due to the less nitrogen in the oxygen-enriched air, thus the oil absorption unit has a reduced oil consumption, but more steam is needed in the feed to control the temperature in the catalyst bed due to the reduced nitrogen amount in the feed.

CN103964996A disclosed an energy-saving process for produce butadiene by oxidative dehydrogenation of butylene with a primary target of reducing the steam consumption during the reaction, wherein a multi-stage fixed bed in series is used, and the reaction heat is recovered via intermediate heat exchanger(s).

CN103964998A disclosed a process for improving the yield of butadiene during the oxidative dehydrogenation of butylene, wherein a multi-stage fixed bed in series is used with all the steam being fed into the first stage of the fixed bed and the feed comprising butylene and the oxygen-comprising gas being fed to each stage of the fixed bed respectively and proportionally, wherein each stage of the fixed bed is packed with layers of various catalysts having different activities for converting different butylene isomers, thus improving the total conversion of butylene and the yield of butadiene.

CN104772081A disclosed a process for catalyst-packing a multi-stage adiabatic fixed bed for producing butadiene by oxidative dehydrogenation of butylene, wherein a multi-stage adiabatic fixed bed in series is used and each stage of the adiabatic fixed bed comprises two reaction zones, which are packed with different catalyst respectively, thus converting butylene to butadiene better and improving the total conversion of butylene and the yield of butadiene.

With regard to the catalytic reaction for producing butadiene by oxidative dehydrogenation of butylene, the adiabatic fixed bed widely used in the prior art is found still with problems such as higher steam consumption, higher power consumption of the compressor, higher load of the oil absorption unit and the like, after comprehensively estimating the total energy consumption of the reaction system and the post treatment system (including heat recovery, water scrubbing, compression of the reaction gas, oil absorption-desorption and the like). Thus, it is still desirable to further reduce the total energy consumption of the process to improve the economy thereof.

SUMMARY OF THE INVENTION

The present invention is related to a process for producing butadiene by oxidative dehydrogenation of butylene, particularly to a process for producing butadiene by oxidative dehydrogenation of butylene using an adiabatic fixed bed.

Regarding the prior art, the present invention makes further adjustments and optimizations of the process conditions for producing butadiene by oxidative dehydrogenation of butylene using multi-stage adiabatic fixed bed, thereby further reducing the total energy consumption of the process and improving the economy of the process.

Thus, the present invention provides a process for producing butadiene by oxidative dehydrogenation of butylene, comprising:

a reaction stage, wherein a multi-stage adiabatic fixed bed in series is used, wherein in the first stage of the adiabatic fixed bed, a reaction feed comprising butylene, oxygen-comprising gas and water as well as a separately fed diluent, being nitrogen and/or carbon dioxide, is reacted in the presence of a catalyst, and in the subsequent stage(s) of the adiabatic fixed bed, butylene, oxygen-comprising gas and water are fed to each stage and reacted therein in the presence of a catalyst, wherein the molar ratio between the separately fed diluent in the first stage of the adiabatic fixed bed and the oxygen of all the oxygen-comprising gases fed in the subsequent stage(s) of the adiabatic fixed bed is in the range of 0.1-3.76, preferably in the range of 0.16-3.76, more preferably in the range of 0.3-3.76, wherein the oxygen-comprising gas is air, oxygen-enriched air or oxygen, and at least one of all the oxygen-comprising gases fed in the subsequent stage(s) of the adiabatic fixed bed is oxygen-enriched air or oxygen, and the oxygen-enriched air has a oxygen concentration of at least 25 vol %, preferably at least 28 vol %, and more preferably at least 35 vol %; and a post treatment stage, wherein the effluent from the last stage of the adiabatic fixed bed is treated to obtain a product butadiene.

According to the present invention, wherein in the reaction stage in the multi-stage adiabatic fixed bed:

for the first stage of the adiabatic fixed bed, butylene and water are fed in gaseous phase, oxygen-comprising gas is fed as air, for the subsequent stage(s) of the adiabatic fixed bed, butylene is fed in liquid or gaseous phase, water is fed in liquid phase, wherein of the reaction feed to the first stage of the adiabatic fixed bed the molar ratio between butylene and the separately fed diluent is in the range of 1:0.004-1:20, preferably in the range of 1:0.05-1:18, more preferably in the range of 1:0.5-1:12.5, and of the reaction feed to each stage of the adiabatic fixed bed the molar ratio between butylene, oxygen and water is in the range of 1.0:0.4:2.0-1.0:1.0:30, preferably in the range of 1.0:0.5:4.0-1.0:1.0:28, more preferably in the range of 1.0:0.5:6.0-1.0:0.85:25.

According to the present invention, wherein the feed of butylene primarily comprises n-butylene. N-butylene can be 1-butylene, cis-2-butylene and trans-2-butylene, and all the three isomers can be oxidized and dehydrogenated to form butadiene in the presence of a catalyst. Thus, the feed of butylene used in the present invention can comprise any mixture of 1-butylene, cis-2-butylene and trans-2-butylene.

Based on the sources of the feed, the feed of butylene may comprise some impurities such as carbon monoxide, carbon dioxide, methanol, ethanol, aldehyde, acetylene, propyne, n-butane, butyne, vinyl acetylene, iso-butane, iso-butylene, C5 hydrocarbons, C6 hydrocarbons, butadiene and the like. In order to reduce the associated separation cost and to facilitate the oxidative dehydrogenation of butylene, it is desirable that the feed of butylene comprises n-butylene at a concentration as high as possible, e. g, the concentration of n-butylene may be of at least 40.0 vol %, preferably of at least 60.0 vol %, more preferably of at least 80.0 vol %, and most preferably of at least 90.0 vol %.

According to the present invention, wherein the feed of butylene may comprise n-butylene at a concentration in the range of 40.0-100.0 vol %, preferably in the range of 60.0-100.0 vol %, and more preferably in the range of 80.0-100.0 vol %.

According to the present invention, wherein the feed of oxygen-comprising gas can be air, oxygen-enriched air or oxygen, wherein the oxygen-enriched air may have a oxygen concentration of at least 25 vol %, preferably at least 28 vol %, and more preferably at least 35 vol %.

According to the present invention, wherein of the reaction feed to the first stage of the adiabatic fixed bed, the oxygen-comprising gas may be air, oxygen-enriched air or oxygen, and preferably air because in such a case air separation is not needed and the nitrogen introduced together with the air can be also used as the diluent, thus being favorable to cost saving.

According to the present invention, wherein of the reaction feed to the subsequent stage(s) of the adiabatic fixed bed, the oxygen-comprising gas may be air, oxygen-enriched air or oxygen, and at least one of all the oxygen-comprising gases fed in the subsequent stage(s) of the adiabatic fixed bed is oxygen-enriched air or oxygen, preferably all the oxygen-comprising gases fed in the subsequent stage(s) of the adiabatic fixed bed are oxygen, because when all the oxygen-comprising gases fed in the subsequent stage(s) of the adiabatic fixed bed are oxygen, more liquid water can be fed in the subsequent stage(s) of the adiabatic fixed bed to remove the reaction heat from the catalyst bed, thus more reaction heat can be recovered to improved the reactor's economy.

Furthermore, according to the present invention, wherein "the molar ratio between the separately fed diluent in the first stage of the adiabatic fixed bed and the oxygen of all the oxygen-comprising gases fed in the subsequent stage(s) of the adiabatic fixed bed" needs to be controlled, particularly, only "the molar ratio between the separately fed diluent in the first stage of the adiabatic fixed bed and all the oxygen fed in the subsequent stage(s) of the adiabatic fixed bed" needs to be controlled when all the oxygen-comprising gases fed in the subsequent stage(s) of the adiabatic fixed bed are fed as oxygen, then the steam amount to be fed to the first stage of the adiabatic fixed bed can be reduced very well, thus saving the steam and improving the energy consumption.

According to the present invention, wherein the feed of water can be steam or liquid water as usually used in the art, wherein of the reaction feed to the first stage of the adiabatic fixed bed, due to that at the beginning of the reaction the reaction feed needs to be preheated to a temperature such as about 300° C., steam is preferred and usually is heat exchanged with the effluent from the last stage of the adiabatic fixed bed to be overheated, then the overheated steam is mixed with butylene, oxygen-comprising gas and diluent and reached a predetermined temperature to be converted in the catalyst bed of the first stage of the adiabatic fixed bed; and of the reaction feed to the subsequent stage(s) of the adiabatic fixed bed, due to that the oxidative dehydrogenation of butylene is an exothermic reaction as whole, the effluent from the preceding stage of the adiabatic fixed bed needs to be cooled, liquid water is preferred and can function as a cooling agent at the same time, thus the process parameters can be controlled rationally and the energy consumption can be reduced again.

According to the present invention, wherein the diluent is separately fed to the first stage of the adiabatic fixed bed only. The diluent can be any suitable diluents used in the art, for example, the diluents can be nitrogen and/or carbon dioxide, preferably carbon dioxide or a mixture of carbon dioxide and nitrogen. Generally, no diluent is fed separately to the subsequent stage(s) of the adiabatic fixed bed, however, the oxygen-comprising gases fed to the subsequent stage(s) of the adiabatic fixed bed may introduce some diluents such as nitrogen therewith at a limited and controllable amount. Herein, it is noted that the diluents used in the present invention do not comprise water.

According to the present invention, as the diluent for the reaction carbon dioxide or a mixture of carbon dioxide and nitrogen is preferred because there is more or less side reactions that produce carbon dioxide in the process of the oxidative dehydrogenation of butylene to butadiene, the presence of carbon dioxide can inhibit the side reactions to some extent, thereby advantageously improving the selectivity and yield of the target product butadiene.

According to the present invention, wherein the multi-stage adiabatic fixed bed can be the multi-stage adiabatic fixed bed as usually used in the art, for example, the multi-stage adiabatic fixed bed can comprise two- or three-stage adiabatic fixed bed in series, wherein each stage of the adiabatic fixed bed can be arranged in a same reactor or separate reactors respectively, and each stage of the adiabatic fixed bed can be an axial fixed bed, a radial fixed bed or an axial-radial fixed bed.

According to the present invention, wherein an inlet feed heat exchanger can be provided for the first stage of the adiabatic fixed bed to preheat those feed components such as butylene, oxygen-comprising gases (e.g. air, oxygen-enriched air or oxygen), steam, diluent and the like to a temperature such as about 300° C., and the steam is usually heat exchanged with the effluent from the last stage of the adiabatic fixed bed to be overheated, then the overheated steam is mixed with butylene, oxygen-comprising gas and diluent and reached a predetermined temperature to be converted in the catalyst bed of the first stage of the adiabatic fixed bed, thus the reaction feed to the first stage of the adiabatic fixed bed is advantageously reached the predetermined temperature to facilitate the oxidative dehydrogenation of butylene in the first stage of the adiabatic fixed bed.

According to the present invention, wherein intermediate feed mixer(s) or intermediate feed distributor(s) are provided between the stages of the adiabatic fixed bed instead of heat exchanger(s). Herein, the intermediate feed mixer and the intermediate feed distributor can be interchangeable, because as designed according to the present invention the effluent from the preceding stage of the adiabatic fixed bed can be directly mixed with the feed to the subsequent stage of the adiabatic fixed bed, thereby controlling the feeding conditions for the subsequent stage of the adiabatic fixed bed. For example, by quenching and mixing the effluent from the preceding stage of the adiabatic fixed bed with those feed components such as butylene, liquid water and oxygen-comprising gas fed to the subsequent stage of the adiabatic fixed bed, the reaction heat of the preceding stage of the adiabatic fixed bed can be utilized sufficiently and the temperature of the reaction feed to the subsequent stage of the adiabatic fixed bed can be controlled very well.

According to the present invention, wherein the intermediate feed mixer(s) or intermediate feed distributor(s) provided between the stages of the adiabatic fixed bed can be any suitable intermediate feed mixer or intermediate feed distributor as usually used in the art, for example, the intermediate feed mixer can be a static mixer, and the intermediate feed distributor can be a gas-liquid twin-fluid nozzles arranged in the form of multiple branches and/or multiple circles, and with such an intermediate feed distributor those feed components can be uniformly distributed within the adiabatic fixed bed, thereby the oxidative dehydrogenation of the butylene can be carried out very effectively.

According to the present invention, wherein the process conditions such as the temperature, pressure and gas hourly space velocity in each stage of the multi-stage adiabatic fixed bed can be suitably controlled by those skilled in the art.

Specifically, according to the present invention, in each stage of the adiabatic fixed bed, the temperature can be in the range of 260.0-700.0° C., preferably in the range of 270.0-680.0° C., more preferably in the range of 280.0-600.0° C., the pressure can be in the range of 0.010-0.500 MPaG, preferably in the range of 0.010-0.300 MPaG, more preferably in the range of 0.010-0.200 PaG, and the butylene can be fed at a gas hourly space velocity in the range of 150-500 $h^{-1}$, preferably in the range of 180-450 $h^{-1}$, more preferably in the range of 180-350 $h^{-1}$.

According to the present invention, wherein the catalyst in each stage of the adiabatic fixed bed can be any suitable catalyst for oxidative dehydrogenation of butylene to butadiene as usually used in the art.

Specifically, according to the present invention, the catalyst for oxidative dehydrogenation of butylene can be an iron based catalyst as usually used in the art. The iron based catalyst can comprise iron, magnesium, oxygen and further elements, which further elements comprise one or more elements selected from the group consisting of barium (Ba), calcium (Ca), nickel (Ni), cobalt (Co), copper (Cu), chromium (Cr), phosphorus (P), silicon (Si), aluminium (Al), vanadium (V), titanium (Ti), zinc (Zn), molybdenum (Mo), tin (Sn), stibium (Sb), zirconium (Zr), manganese (Mn) and rare earth elements. The iron based catalyst comprises 48.80-60.50 wt % iron (Fe), 0.01-18.00 wt % magnesium (Mg) and 0-5.00 wt % further elements, and the balance is oxygen, based on the total weight of the iron based catalyst.

As known in the art, the iron based catalyst is generally prepared by a precipitation process through a neutralization reaction between acid and alkali, wherein the basic solution can be a solution of one or more selected from the group consisting of $Na_2CO_3$, $K_2CO_3$, $KHCO_3$, $NaHCO_3$, NaOH, KOH, $NH_3$, $NH_4HCO_3$ and urea, the acidic solution can be a nitric acid solution with one or more steel, iron powder, ferric nitrate being dissolved therein, and these two solutions reacted to form precipitates, which precipitates can be formed into a particulate catalyst, for example, in the form of cylinder or clover, through a series of processes including filtering, washing, drying, roasting, tabletting and the like, and the particulate catalyst can be used in the oxidative dehydrogenation of butylene.

According to the present invention, wherein in the post treatment stage the effluent from the last stage of the adiabatic fixed bed is subjected to various post treatments as usually used in the art. For example, the post treatments can comprise heat recovery, water scrubbing, gas compression, oil absorption-desorption, butadiene extraction and the like in sequence to obtain a final product butadiene, wherein after gas compression another water scrubbing is carried out optionally.

Over the prior art, in the process for producing butadiene by oxidative dehydrogenation of butylene of the present invention, wherein the diluent is separately fed to the first stage of the adiabatic fixed bed only, and the molar ratio between the separately fed diluent and the oxygen of all the oxygen-comprising gases fed in the subsequent stage(s) of the adiabatic fixed bed is controlled within a range, so that to reduce the steam consumption and reach a lower total energy consumption with no increasing or even reducing the compressor power consumption and the load of the oil absorption unit.

BRIEF DESCRIPTION OF FIGURES

Now the present invention is further described with reference to the following figures, to which the present invention should not be limited anyway, wherein.

In each figure, same numerals refer to same parts or components, wherein all the numerals mean as following.

1. feed of steam to the first stage of the adiabatic fixed bed; 2. feed heat exchanger; 3. feed of butylene to the first stage of the adiabatic fixed bed; 4. feed of oxygen-comprising gas to the first stage of the adiabatic fixed bed; 5. feed of diluent to the first stage of the adiabatic fixed bed; 6. feed mixer of the first stage of the adiabatic fixed bed; 7. reaction feed to the first stage of the adiabatic fixed bed; 8. catalyst bed of the first stage of the adiabatic fixed bed; 9. effluent from the first stage of the adiabatic fixed bed; 10. liquid water to the second stage of the adiabatic fixed bed; 11. feed of butylene to the second stage of the adiabatic fixed bed; 12. first intermediate feed mixer of the second stage of the adiabatic fixed bed; 13. feed of oxygen-comprising gas to the second stage of the adiabatic fixed bed; 14. second intermediate feed mixer of the second stage of the adiabatic fixed bed; 15. reaction feed to the second stage of the adiabatic fixed bed; 16. catalyst bed of the second stage of the adiabatic fixed bed; 17. effluent from the second stage of the adiabatic fixed bed; 18. heat exchanged effluent from the second stage of the adiabatic fixed bed; 19. intermediate feed distributor of the second stage of the adiabatic fixed bed; 20. collecting channel of the first stage of the adiabatic fixed bed; 21. annular channel of the first stage of the adiabatic fixed bed; 22. central flow channel of the second stage of the adiabatic fixed bed; 23. annular channel of the second stage of the adiabatic fixed bed.

DETAILED DESCRIPTION

The present invention is related to a process for producing butadiene by oxidative dehydrogenation of butylene, particularly to a process for producing butadiene by oxidative dehydrogenation of butylene using an adiabatic fixed bed.

In the process for producing butadiene by oxidative dehydrogenation of butylene, two hydrogen atoms are removed from one butylene molecular and combined with one oxygen atom to form one butadiene molecular and one water molecular in the presence of catalyst, wherein the oxidation makes the endothermal dehydrogenation of butylene an exothermal reaction, so that the whole reaction can be carried out at a lower temperature, thereby reducing the energy consumption of the reaction. The oxidative dehydrogenation of butylene is reacted according to the following equation: $2C_4H_8+O_2 \rightarrow 2C_4H_6+2H_2O+126$ kJ/mol.

Along with the oxidative dehydrogenation of butylene, a limited amount of butylene or butadiene is oxidized deeply to form carbon monoxide, carbon dioxide as well as organic oxygenates such as aldehydes, ketones, furans and the like. The side reactions are mainly as following:

$$C_4H_8+4O_2 \rightarrow 4CO+4H_2O+1268 \text{ kJ/mol};$$

$$C_4H_8+6O_2 \rightarrow 4CO_2+4H_2O+2553 \text{ kJ/mol};$$

$$2C_4H_8+3O_2 \rightarrow 2C_4H_4O+4H_2O+251 \text{ kJ/mol}.$$

The oxidative dehydrogenation of butylene to butadiene is highly exothermal. In the case where an adiabatic fixed bed being used, a certain amount of steam is generally used to remove the reaction heat effectively, thereby the reaction being carried out at an appropriate temperature.

According to the present invention, the oxidative dehydrogenation of butylene to butadiene is carried out in the presence of an iron based catalyst, which may comprise iron, magnesium, oxygen and further elements, which further elements may comprise one or more elements selected from the group consisting of barium (Ba), calcium (Ca), nickel (Ni), cobalt (Co), copper (Cu), chromium (Cr), phosphorus (P), silicon (Si), aluminium (Al), vanadium (V), titanium (Ti), zinc (Zn), molybdenum (Mo), tin (Sn), stibium (Sb), zirconium (Zr), manganese (Mn) and rare earth elements. The iron based catalyst comprises 48.80-60.50 wt % iron (Fe), 0.01-18.00 wt % magnesium (Mg) and 0-5.00 wt % further elements, and the balance is oxygen, based on the total weight of the iron based catalyst.

EXAMPLES

Now the present invention is further detailedly described with reference to the examples and the comparative examples, however, the present invention should not be limited to those examples anyway.

In all of the examples and the comparative examples:

The reactor is a two-stage adiabatic fixed bed with an intermediate feed quench for controlling the feeding conditions in the second stage of the adiabatic fixed bed, wherein each adiabatic fixed bed is packed with a catalyst at a volume of 7 m³, and each adiabatic fixed bed may be axial, radial or axial-radial fixed bed and is specifically arranged in each example.

The catalyst packed in each adiabatic fixed bed is an iron based catalyst in the form of cylinder (5 mm×5 mm), which iron based catalyst comprises 57.70 wt % iron (Fe), 6.32 wt % magnesium (Mg), 1.22 wt % calcium (Ca), 0.51 wt % nickel (Ni) and 2.04 wt % phosphorus (P), and the balance is oxygen.

The compositions of all streams including the feeds and the effluents are determined by Gas Chromatography.

The temperatures for the feeds and the effluents of each stage of the adiabatic fixed bed are determined by thermocouples provided at the inlet and outlet of each stage of the adiabatic fixed bed and reported as an average of several thermocouples results.

The pressures for the feeds and the effluents of each stage of the adiabatic fixed bed are determined by pressure gauges provided at the inlet and outlet of each stage of the adiabatic fixed bed.

The gas hourly space velocity of butylene for each stage of the adiabatic fixed bed is the volume of butylene in standard state passing over per volume of the catalyst bed per hour.

Total energy consumption is expressed as kilograms of standard oil per ton of butadiene, i.e. kilograms of standard oil corresponding to the energy consumption required for generating one ton of butadiene. This total energy consumption is calculated on the basis of State Standard of the People's Republic of China GB/T 50441-2007 (standard for calculating the energy consumption in petrochemical engineering), wherein the feed preheating system comprises feed heat exchanger, feed of steam, diluent (nitrogen and/or carbon dioxide), oxygen, air, oxygen-enriched air and quenching water, and the post treatment system comprises heat recovery from the last effluent, water scrubbing, compression, oil absorption-desorption and butadiene extraction, and wherein the total energy consumption does not comprise the feed of butylene.

Example 1

Figure 1:
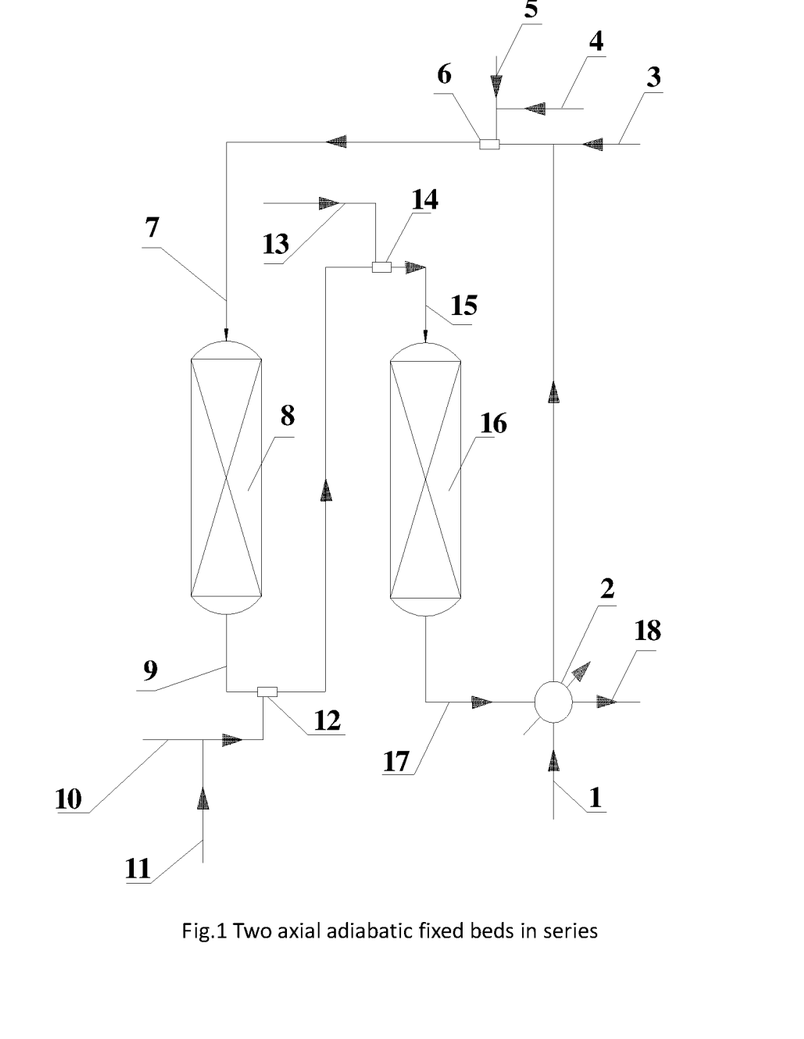
FIG. 1 schematically illustrates a block flow diagram of an embodiment according to the present invention, wherein a reactor comprising two axial adiabatic fixed beds in series is used, and an intermediate feed mixer is provided between the two adiabatic fixed beds.

Example 1 is carried out according to the block flow diagram as shown in FIG. 1, wherein two axial adiabatic fixed beds in series arranged in two separate reaction vessels are used, and an intermediate feed mixer is provided.

The reaction in the first adiabatic fixed bed: after being heat exchanged with the effluent 17 from the second adiabatic fixed bed in the feed heat exchanger 2, feed of steam 1 to the first adiabatic fixed bed is sufficiently mixed with the feed of butylene 3, the feed of oxygen-comprising gas 4 and the feed of diluent 5 in the feed mixer 6 of the first adiabatic fixed bed to form the reaction feed 7 to the first adiabatic fixed bed, wherein the feed of oxygen-comprising gas 4 is air and the feed of diluent 5 is nitrogen, the feed of butylene 3, the feed of air 4 and the feed of steam 1 are fed at a molar ratio as butylene:oxygen:water in the range of 1:0.90:14.41, and the feed of butylene 3 and the feed of diluent 5 are fed at a molar ratio as butylene:nitrogen of 1:1.46. The reaction feed 7 is converted in the catalyst bed 8 of the first adiabatic fixed bed to form the effluent 9 from the first adiabatic fixed bed, wherein the reaction feed 7 has a temperature of 280° C. and a pressure of 0.200 MPaG, the butylene is fed to the catalyst bed 8 of the first adiabatic fixed bed at a gas hourly space velocity of 250 $h^{-1}$, and the effluent 9 has a temperature of 470.5° C. and a pressure of 0.185 MPaG.

The reaction in the second adiabatic fixed bed: liquid water 10 and the feed of butylene 11 are sufficiently mixed with the effluent 9 from the first adiabatic fixed bed in the first feed mixer 12 of the second adiabatic fixed bed, the feed of oxygen-comprising gas 13 to the second adiabatic fixed bed is mixed with the effluent 12 from the first feed mixer in the second feed mixer 14 of the second adiabatic fixed bed to form the reaction feed 15 to the second adiabatic fixed bed, which is converted in the catalyst bed 16 of the second adiabatic fixed bed to form the effluent 17 from the second adiabatic fixed bed, wherein the reaction feed 15 has a temperature of 279.6° C., a pressure of 0.165 MPaG, and a molar ratio of butylene:oxygen:water of 1:0.62:9.35, the butylene is fed to the catalyst bed 16 of the second adiabatic fixed bed at a gas hourly space velocity of 450 $h^{-1}$, the effluent 17 has a temperature of 573.5° C. and a pressure of 0.145 MPaG, and wherein the feed of oxygen-comprising gas 13 is oxygen, and the molar ratio between the feed of diluent 5 to the first adiabatic fixed bed and oxygen in the feed of oxygen-comprising gas 13 to the second adiabatic fixed bed is of 2.0:1.

Post treatment: after being cooled by heat exchanging with the feed of steam 1 to the first adiabatic fixed bed, the effluent 17 becomes the heat exchanged effluent 18 from the second adiabatic fixed bed, which is sequentially subjected to heat recovery, water scrubbing, multi-stage compression, water scrubbing, oil absorption-desorption, butadiene extraction and the like to obtain a finished butadiene finally.

In this example, the conversion of butylene is of 76.43%, the selectivity of butadiene is of 91.51%, the yield of butadiene is of 69.94%, and the energy consumption of the process is of 1200 kg of standard oil per ton of butadiene.

Comparative Example 1

Example 1 was repeated, except that the molar ratio between the feed of diluent 5 to the first adiabatic fixed bed and the oxygen in the feed of oxygen-comprising gas 13 to the second adiabatic fixed bed is of 4.00:1.

In this example, the conversion of butylene is of 65.92%, the selectivity of butadiene is of 89.85%, the yield of butadiene is of 59.22%, and the energy consumption of the process is of 1789 kg of standard oil per ton of butadiene.

Example 2

Figure 2:
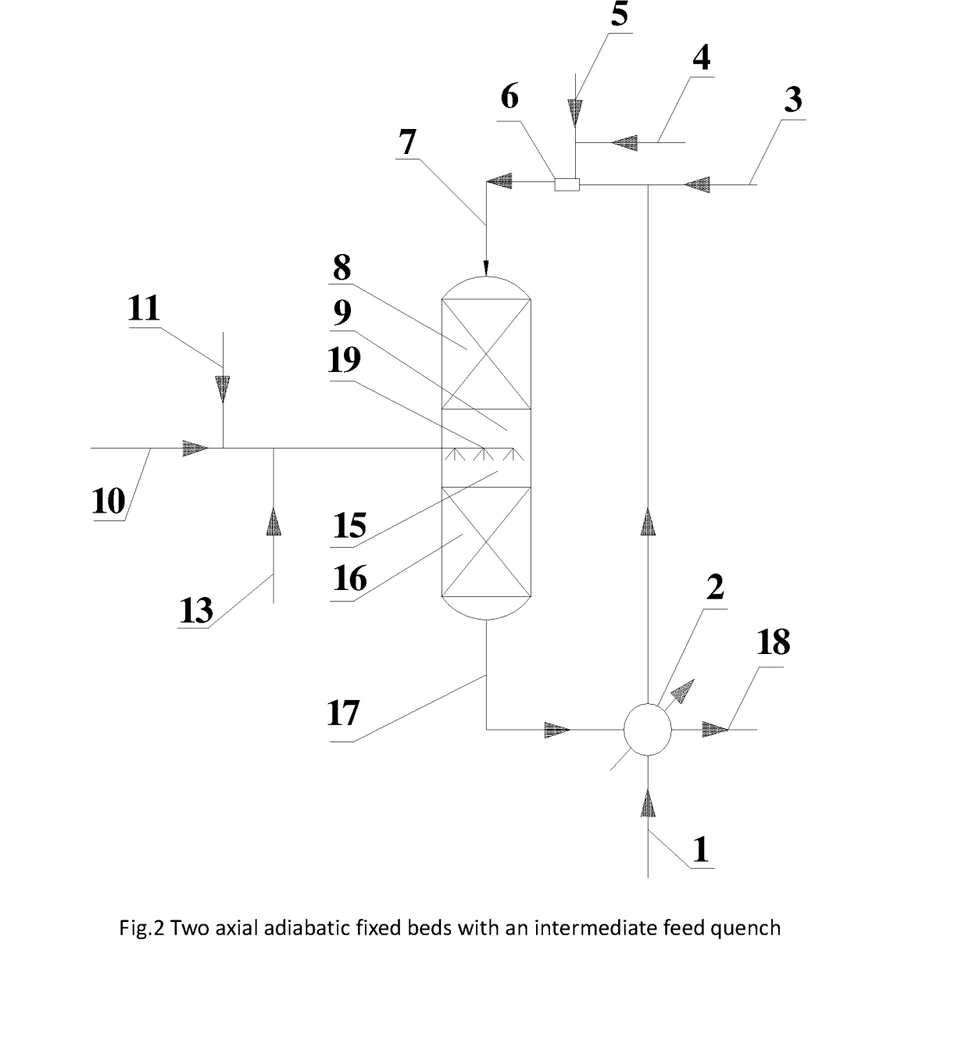
FIG. 2 schematically illustrates a block flow diagram of another embodiment according to the present invention, wherein a reactor comprising two axial adiabatic fixed beds in series is used, and an intermediate feed distributor is provided between the two adiabatic fixed beds.

Example 2 is carried out according to the block flow diagram as shown in FIG. 2, wherein two axial adiabatic fixed beds in series arranged in one reaction vessel are used, and twin-fluid nozzles arranged in the form of multiple circles are used as the intermediate feed distributor, which evenly distributes the reaction feed to the second adiabatic fixed bed.

The reaction in the first adiabatic fixed bed: after being heat exchanged with the effluent 17 from the second adiabatic fixed bed in the feed heat exchanger 2, feed of steam 1 to the first adiabatic fixed bed is sufficiently mixed with the feed of butylene 3, the feed of oxygen-comprising gas 4 and the feed of diluent 5 in the feed mixer 6 of the first adiabatic fixed bed to form the reaction feed 7 to the first adiabatic fixed bed, wherein the feed of oxygen-comprising gas 4 is air and the feed of diluent 5 is carbon dioxide, the feed of butylene 3, the feed of air 4 and the feed of steam 1 are fed at a molar ratio as butylene:oxygen:water of 1:0.50:13.47, and the feed of butylene 3 and the feed of diluent 5 are fed at a molar ratio as butylene:carbon dioxide of 1:1.61. The reaction feed 7 is converted in the catalyst bed 8 of the first adiabatic fixed bed to form the effluent 9 from the first adiabatic fixed bed, wherein the reaction feed 7 has a temperature of 400° C. and a pressure of 0.150 MPaG, the butylene is fed to the catalyst bed 8 of the first adiabatic fixed bed at a gas hourly space velocity of 180 $h^{-1}$, and the effluent 9 has a temperature of 580° C. and a pressure of 0.135 MPaG.

The reaction in the second adiabatic fixed bed: liquid water 10, the feed of butylene 11 and the feed of oxygen-comprising gas 13 are distributed via the twin-fluid nozzles arranged in the form of multiple circles of the intermediate feed distributor 19 of the second adiabatic fixed bed and sufficiently mixed and quenched with the effluent 9 from the first adiabatic fixed bed to form the reaction feed 15 to the second adiabatic fixed bed, which is converted in the catalyst bed 16 of the second adiabatic fixed bed to form the effluent 17 from the second adiabatic fixed bed, wherein the reaction feed 15 has a temperature of 275.5° C. and a pressure of 0.115 MPaG, and a molar ratio of butylene:oxygen:water of 1:0.600:6.56, the butylene is fed to the catalyst bed 16 of the second adiabatic fixed bed at a gas hourly space velocity of 450 h⁻¹, the effluent 17 has a temperature of 602.0° C. and a pressure of 0.095 MPaG, and wherein the feed of oxygen-comprising gas 13 to the second adiabatic fixed bed is an oxygen-enriched air comprising 65 vol % nitrogen and 35 vol % oxygen, and the molar ratio between the feed of diluent 5 to the first adiabatic fixed bed and the oxygen in the feed of oxygen-comprising gas 13 to the second adiabatic fixed bed is of 1.08:1.

Post treatment: after being cooled by heat exchanging with the feed of steam 1 to the first adiabatic fixed bed, the effluent 17 becomes the heat exchanged effluent 18 from the second adiabatic fixed bed, which is sequentially subjected to heat recovery, water scrubbing, multi-stage compression, water scrubbing, oil absorption-desorption, butadiene extraction and the like to obtain a finished butadiene finally.

In this example, the conversion of butylene is of 74.09%, the selectivity of butadiene is of 92.55%, the yield of butadiene is of 68.58%, and the energy consumption of the process is of 1127 kg of standard oil per ton of butadiene.

Comparative Example 2

Example 2 was repeated, except that the molar ratio between the feed of diluent 5 to the first adiabatic fixed bed and the oxygen in the feed of oxygen-comprising gas 13 to the second adiabatic fixed bed is of 5.04:1.

In this example, the conversion of butylene is of 71.67%, the selectivity of butadiene is of 91.44%, the yield of butadiene is of 65.53%, and the energy consumption of the process is of 2657 kg of standard oil per ton of butadiene.

Example 3

Figure 3:
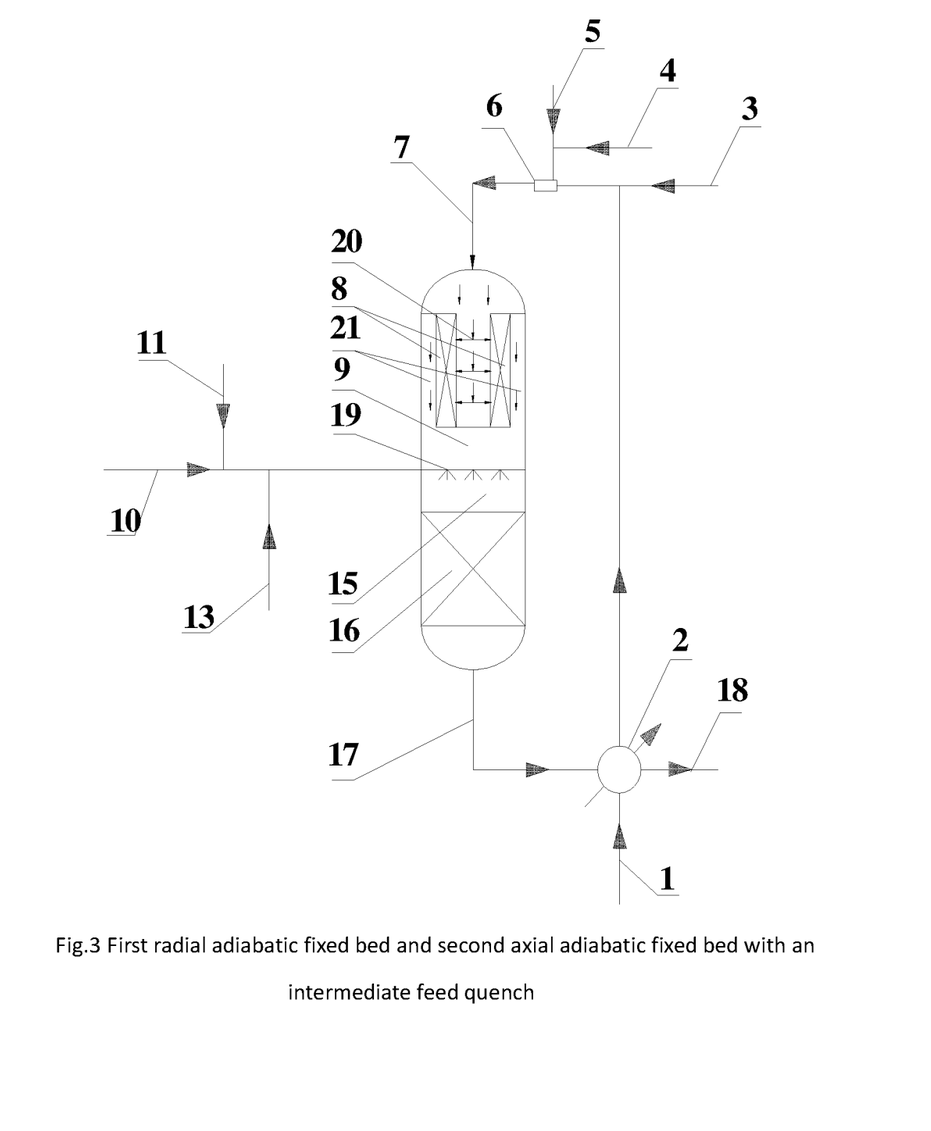
FIG. 3 schematically illustrates a block flow diagram of another embodiment according to the present invention, wherein a reactor comprising first radial adiabatic fixed bed and second axial adiabatic fixed bed in series is used, and an intermediate feed distributor is provided between the two adiabatic fixed beds.

Example 3 is carried out according to the block flow diagraph as shown in FIG. 3, wherein first radial adiabatic fixed bed and second axial adiabatic fixed bed in series arranged in one reaction vessel are used, and twin-fluid nozzles arranged in the form of multiple branches are used as the intermediate feed distributor, which evenly distributes the reaction feed to the second adiabatic fixed bed.

The reaction in the first adiabatic fixed bed: after being heat exchanged with the effluent 17 from the second adiabatic fixed bed in the feed heat exchanger 2, feed of steam 1 to the first adiabatic fixed bed is sufficiently mixed with the feed of butylene 3, the feed of oxygen-comprising gas 4 and the feed of diluent 5 in the feed mixer 6 of the first adiabatic fixed bed to form the reaction feed 7 to the first adiabatic fixed bed, wherein the feed of oxygen-comprising gas 4 is air and the feed of diluent 5 is carbon dioxide, the feed of butylene 3, the feed of air 4 and the feed of steam 1 are fed at a molar ratio as butylene:oxygen:water of 1:0.543:12.07, and the feed of butylene 3 and the feed of diluent 5 are fed at a molar ratio as butylene:carbon dioxide of 1:2.35. The reaction feed 7 to the first adiabatic fixed bed is introduced in radial direction into the catalyst bed 8 of the first adiabatic fixed bed via the collecting channel 20 of the first adiabatic fixed bed to be converted therein and then form the effluent 9 leaving via the annular channel 21 of the first adiabatic fixed bed, wherein the reaction feed 7 has a temperature of 340° C. and a pressure of 0.065 MPaG, the butylene is fed to the catalyst bed 8 of the first adiabatic fixed bed at a gas hourly space velocity of 280 h⁻¹, and the effluent 9 has a temperature of 530.0° C. and a pressure of 0.050 MPaG.

The reaction in the second adiabatic fixed bed: liquid water 10, the feed of butylene 11 and the feed of oxygen-comprising gas 13 are atomized and distributed via the twin-fluid nozzles arranged in the form of multiple branches of the intermediate feed distributor 19 of the second adiabatic fixed bed and sufficiently mixed and quenched with the effluent 9 from the first adiabatic fixed bed to form the reaction feed 15 to the second adiabatic fixed bed, which is introduced in axial direction into the catalyst bed 16 of the second adiabatic fixed bed to be converted therein to form the effluent 17 from the second adiabatic fixed bed, wherein the reaction feed 15 has a temperature of 349.9° C. and a pressure of 0.030 MPaG, and a molar ratio of butylene:oxygen:water of 1:0.649:14.13, the butylene is fed to the catalyst bed 16 of the second adiabatic fixed bed at a gas hourly space velocity of 290 h⁻¹, the effluent 17 has a temperature of 544.3° C. and a pressure of 0.010 MPaG, and wherein the feed of oxygen-comprising gas 13 to the second adiabatic fixed bed is oxygen, and the molar ratio between the feed of diluent 5 to the first adiabatic fixed bed and the oxygen in the feed of oxygen-comprising gas 13 to the second adiabatic fixed bed is of 3.76:1.

Post treatment: after being cooled by heat exchanging with the feed of steam 1 to the first adiabatic fixed bed, the effluent 17 becomes the heat exchanged effluent 18 from the second adiabatic fixed bed, which is sequentially subjected to heat recovery, water scrubbing, multi-stage compression, water scrubbing, oil absorption-desorption, butadiene extraction and the like to obtain a finished butadiene finally.

In this example, the conversion of butylene is of 81.29%, the selectivity of butadiene is of 92.47%, the yield of butadiene is of 75.17%, and the energy consumption of the process is of 1499 kg of standard oil per ton of butadiene.

Comparative Example 3

Example 3 was repeated, except that the molar ratio between the feed of diluent 5 to the first adiabatic fixed bed and the oxygen in the feed of oxygen-comprising gas 13 to the second adiabatic fixed bed is of 6.00:1.

In this example, the conversion of butylene is of 74.06%, the selectivity of butadiene is of 91.52%, the yield of butadiene is of 67.78%, and the energy consumption of the process is of 2094 kg of standard oil per ton of butadiene.

Example 4

Figure 4:
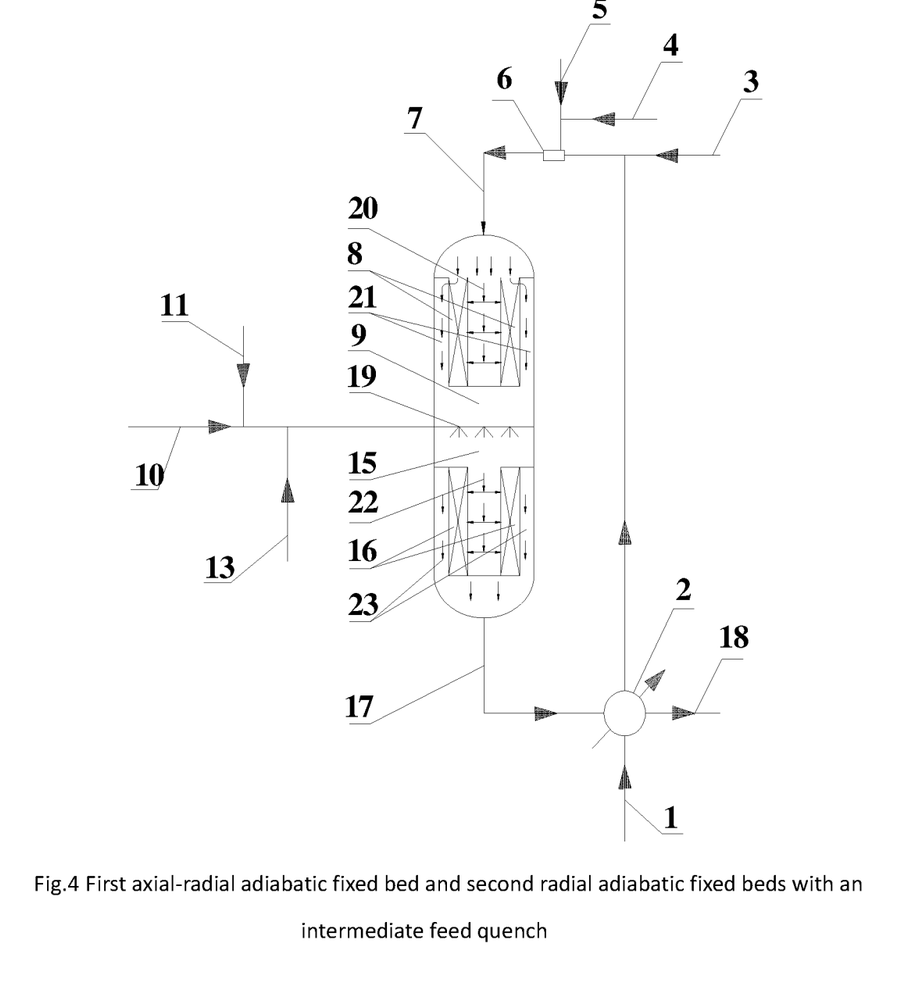
FIG. 4 schematically illustrates a block flow diagram of yet another embodiment according to the present invention, wherein a reactor comprising first axial-radial adiabatic fixed bed and second radial adiabatic fixed bed in series is used, and an intermediate feed distributor is provided between the two adiabatic fixed beds.

Example 4 is carried out according to the block flow diagraph as shown in FIG. 4, wherein first axial-radial adiabatic fixed bed and second radial adiabatic fixed bed in series arranged in one reaction vessel are used, and twin-fluid nozzles arranged in the form of multiple circles are used as the intermediate feed distributor, which evenly distributes the reaction feed to the second adiabatic fixed bed.

The reaction in the first adiabatic fixed bed: after being heat exchanged with the effluent 17 from the second adiabatic fixed bed in the feed heat exchanger 2, feed of steam 1 to the first adiabatic fixed bed is sufficiently mixed with the feed of butylene 3, the feed of oxygen-comprising gas 4 and the feed of diluent 5 in the feed mixer 6 of the first adiabatic fixed bed to form the reaction feed 7 to the first adiabatic fixed bed, wherein the feed of oxygen-comprising gas 4 is air and the feed of diluent 5 is a mixture of nitrogen and carbon dioxide comprising 10.0 vol % nitrogen and 90.0 vol % carbon dioxide, the feed of butylene 3, the feed of air 4 and the feed of steam 1 are fed at a molar ratio as butylene:oxygen:water of 1:0.600:19.26, and the feed of butylene 3 and the feed of diluent 5 are fed at a molar ratio as butylene:(nitrogen+carbon dioxide) of 1:0.11. Part of the reaction feed 7 to the first adiabatic fixed bed is introduced in radial direction into the catalyst bed 8 of the first adiabatic fixed bed via the collecting channel 20 of the first adiabatic fixed bed to be converted therein and the other part of the reaction feed 7 is introduced in axial direction into the catalyst bed 8 to be converted therein, and then form the effluent 9 leaving via the annular channel 21 of the first adiabatic fixed bed, wherein the reaction feed 7 has a temperature of 300° C. and a pressure of 0.100 MPaG, the butylene is fed to the catalyst bed 8 of the first adiabatic fixed bed at a gas hourly space velocity of 210 h$^{-1}$, and the effluent 9 has a temperature of 461.3° C. and a pressure of 0.085 MPaG.

The reaction in the second adiabatic fixed bed: liquid water 10, the feed of butylene 11 and the feed of oxygen-comprising gas 13 are atomized and distributed via the twin-fluid nozzles arranged in the form of multiple circles of the intermediate feed distributor 19 of the second adiabatic fixed bed and sufficiently mixed and quenched with the effluent 9 from the first adiabatic fixed bed to form the reaction feed 15 to the second adiabatic fixed bed, which is introduced in radial direction into the catalyst bed 16 of the second adiabatic fixed bed via the collecting channel 22 of the second adiabatic fixed bed to be converted therein, then form the effluent 17 leaving via the annular channel 23 of the second adiabatic fixed bed, wherein the reaction feed 15 has a temperature of 290.0° C. and a pressure of 0.065 MPaG, and a molar ratio of butylene:oxygen:water of 1:0.655:18.83, the butylene is fed to the catalyst bed 16 of the second adiabatic fixed bed at a gas hourly space velocity of 245 h$^{-1}$, the effluent 17 has a temperature of 465.2° C. and a pressure of 0.045 MPaG, and wherein the feed of oxygen-comprising gas 13 to the second adiabatic fixed bed is an oxygen-enriched air comprising 72 vol % nitrogen and 28 vol % oxygen, and the molar ratio between the feed of diluent 5 to the first adiabatic fixed bed and the oxygen in the feed of oxygen-comprising gas 13 to the second adiabatic fixed bed is of 0.16:1.

Post treatment: after being cooled by heat exchanging with the feed of steam 1 to the first adiabatic fixed bed, the effluent 17 becomes the heat exchanged effluent 18 from the second adiabatic fixed bed, which is sequentially subjected to heat recovery, water scrubbing, multi-stage compression, water scrubbing, oil absorption-desorption, butadiene extraction and the like to obtain a finished butadiene finally.

In this example, the conversion of butylene is of 79.44%, the selectivity of butadiene is of 92.47%, the yield of butadiene is of 73.46%, and the energy consumption of the process is of 1763 kg of standard oil per ton of butadiene.

Comparative Example 4

Example 4 was repeated, except that the molar ratio between the feed of diluent 5 to the first adiabatic fixed bed and the oxygen in the feed of oxygen-comprising gas 13 to the second adiabatic fixed bed is of 0.08:1.

In this example, the conversion of butylene is of 52.46%, the selectivity of butadiene is of 89.36%, the yield of butadiene is of 46.88%, and the energy consumption of the process is of 1788 kg of standard oil per ton of butadiene.

The associated parameters and the reached technical effects of the examples and the comparative examples are summarized in Table 1, wherein the parameter of "Diluents/oxygen fed in subsequent stages (mol/mol)" refers to the molar ratio between the diluent separately fed to the first stage of the adiabatic fixed bed and the oxygen of the oxygen-comprising gas fed in the second stage of the adiabatic fixed bed.

TABLE 1

The controlled parameters and the results of energy consumption for the examples and the comparative examples

| | Paramenters | | | | |
|---|---|---|---|---|---|
| Ex. No. | Diluents/oxygen fed in subsequent stages (mol/mol) | Conversion of butylene (%) | Selectivity of butadiene (%) | Yield of butadiene (%) | Standard oil/butadiene kg/t |
| Ex. 1 | 2.00 | 76.43 | 91.51 | 69.94 | 1200 |
| Com. Ex. 1 | 4.00 | 65.92 | 89.85 | 59.22 | 1789 |
| Ex. 2 | 1.08 | 74.09 | 92.55 | 68.58 | 1127 |
| Com. Ex. 2 | 5.04 | 71.67 | 91.44 | 65.53 | 2657 |
| Ex. 3 | 3.76 | 81.29 | 92.47 | 75.17 | 1499 |
| Com. Ex. 3 | 6.00 | 74.06 | 91.52 | 67.78 | 2094 |
| Ex. 4 | 0.16 | 79.44 | 92.47 | 73.46 | 1763 |
| Com. Ex. 4 | 0.08 | 52.46 | 89.36 | 46.88 | 1788 |

Based on the data shown in Table 1, by comparing the examples of the present invention and the comparative example, it can be known that according to the present invention the total energy consumption of all the process stages including feed heat exchanger(s), reaction systems as well as heat recovery, water scrubbing, compression, water scrubbing, oil absorption-desorption and butadiene extraction can be reduced with not degraded conversion of butylene, selectivity and yield of butadiene due to the molar ratio between the diluent separately fed to the first stage of the adiabatic fixed bed and the oxygen of all the oxygen-comprising gases fed in the subsequent stage(s) of the adiabatic fixed bed being controlled, thereby improving the process economy.

Thus, the present invention made further improvements to the prior art without reducing the associated process targets such as the conversion of butylene as well as the selectivity and yield of butadiene and the like.

What claimed is:

1. A process for producing butadiene by oxidative dehydrogenation of butylene, comprising:
   a reaction stage, wherein multi-stage adiabatic fixed beds in series are used, wherein in the first stage of the multi-stage adiabatic fixed beds, a reaction feed comprising butylene, oxygen-comprising gas, being air, and water, as well as a separately fed diluent, being carbon dioxide or a mixture of carbon dioxide and nitrogen, with carbon dioxide present in an amount of at least 90.0 vol % in the mixture of carbon dioxide and nitrogen to inhibit side reactions, is reacted in the presence of a catalyst, and in the subsequent stage(s) of the multi-stage adiabatic fixed beds, butylene, oxygen-comprising gas and water are fed to each stage and reacted therein in the presence of a catalyst, wherein a molar ratio between the separately fed diluent in the first stage of the multi-stage adiabatic fixed beds and the oxygen of all the oxygen-comprising gases fed in the subsequent stage(s) of the multi-stage adiabatic fixed beds is in a range of 0.1-3.76, wherein the oxygen-comprising gases fed in the subsequent stage(s) of the multi-stage adiabatic fixed beds is oxygen; and
   a post treatment stage, wherein the effluent from the last stage of the multi-stage adiabatic fixed beds is treated to obtain a product butadiene.

2. The process as claimed in claim 1, wherein in the reaction stage in the multi-stage adiabatic fixed beds:

for the first stage of the multi-stage adiabatic fixed beds, butylene and water are fed in gaseous phase, for the subsequent stage(s) of the multi-stage adiabatic fixed beds, butylene is fed in liquid or gaseous phase, water is fed in liquid phase, wherein the first stage of the multi-stage adiabatic fixed beds is fed with the reaction feed having a molar ratio between butylene and the separately fed diluent in a range of 1:0.004-1:20, and each stage of the multi-stage adiabatic fixed beds is fed with a reaction feed having a molar ratio of butylene to oxygen to water is in a range of 1.0:0.4:2.0-1.0:1.0:30.

3. The process as claimed in claim 2, wherein of the reaction feed to the first stage of the multi-stage adiabatic fixed beds, the water in the gaseous phase is heat exchanged with the effluent from the last stage of the multi-stage adiabatic fixed beds to be overheated, then mixed with butylene, oxygen-comprising gas and diluent and reached a predetermined temperature to be converted in a catalyst bed of the first stage of the multi-stage adiabatic fixed beds.

4. The process as claimed in claim 1, wherein in each stage of the multi-stage adiabatic fixed beds the temperature is independently in a range of 260.0-700.0° C., the pressure is independently in a range of 0.010-0.500 MPaG, and butylene is independently fed at a gas hourly space velocity in a range of 150-500 $h^{-1}$.

5. The process as claimed in claim 1, wherein the butylene fed in each stage of the multi-stage adiabatic fixed beds comprises n-butylene at a concentration of 40.0-100.0 vol %.

6. The process as claimed in claim 1, wherein the catalyst in each stage of the multi-stage adiabatic fixed beds is an iron based catalyst comprising iron, magnesium, oxygen and optional further elements, wherein the optional which further elements comprise one or more elements selected from the group consisting of barium, calcium, nickel, cobalt, copper, chromium, phosphorus, silicon, aluminium, vanadium, titanium, zinc, molybdenum, tin, stibium, zirconium, manganese and rare earth elements, the iron based catalyst comprises 48.80-60.50 wt % iron, 0.01-18.00 wt % magnesium and 0-5.00 wt % optional further elements, and the balance is oxygen, based on the total weight of the iron based catalyst.

7. The process as claimed in claim 1, wherein the multi-stage adiabatic fixed beds comprise two-stage or three-stage adiabatic fixed beds in series, wherein each stage of the multi-stage adiabatic fixed beds is arranged in a same reactor or separate reactors respectively, and each stage of the multi-stage adiabatic fixed beds is an axial fixed bed, a radial fixed bed or an axial-radial fixed bed.

8. The process as claimed in claim 1, wherein an inlet feed heat exchanger is provided for the first stage of the multi-stage adiabatic fixed beds, and intermediate feed mixer(s) or intermediate feed distributor(s) are provided between the stages of the multi-stage adiabatic fixed beds.

9. The process as claimed in claim 1, wherein in the post treatment stage the effluent from the last stage of the multi-stage adiabatic fixed beds is subjected to a post treatment including heat recovery, water scrubbing, gas compression, oil absorption-desorption and butadiene extraction to obtain a final product butadiene.

* * * * *